United States Patent
Boese et al.

(10) Patent No.: US 8,068,581 B2
(45) Date of Patent: Nov. 29, 2011

(54) METHOD FOR REPRESENTING INTERVENTIONAL INSTRUMENTS IN A 3D DATA SET OF AN ANATOMY TO BE EXAMINED AS WELL AS A REPRODUCTION SYSTEM FOR PERFORMING THE METHOD

(75) Inventors: Jan Boese, Eckental (DE); Klaus Klingenbeck, Wüstenstein/Wiesenttal (DE)

(73) Assignee: Siemens Aktiengesellschaft, Munich (DE)

( * ) Notice: Subject to any disclaimer, the term of this patent is extended or adjusted under 35 U.S.C. 154(b) by 147 days.

(21) Appl. No.: 12/507,343

(22) Filed: Jul. 22, 2009

(65) Prior Publication Data

US 2010/0020926 A1    Jan. 28, 2010

(30) Foreign Application Priority Data

Jul. 25, 2008   (DE) .................. 10 2008 034 686

(51) Int. Cl.
*G01N 23/04* (2006.01)
(52) U.S. Cl. .................. 378/62; 378/98.12; 378/205
(58) Field of Classification Search .................. 378/36, 378/62, 98.12, 205
See application file for complete search history.

(56) References Cited

U.S. PATENT DOCUMENTS

| | | | |
|---|---|---|---|
| 6,317,621 B1 * | 11/2001 | Graumann et al. | 600/424 |
| 6,351,513 B1 * | 2/2002 | Bani-Hashemi et al. | 378/8 |
| 6,672,165 B2 | 1/2004 | Auner et al. | |
| 6,923,768 B2 * | 8/2005 | Camus et al. | 600/463 |
| 7,343,195 B2 * | 3/2008 | Strommer et al. | 600/424 |
| 7,400,431 B2 | 7/2008 | Schwerdtner et al. | |
| 7,519,414 B2 * | 4/2009 | Mitschke et al. | 600/424 |
| 7,697,973 B2 * | 4/2010 | Strommer et al. | 600/424 |
| 2003/0181809 A1 | 9/2003 | Hall | |
| 2006/0050340 A1 | 3/2006 | Haussler et al. | |
| 2008/0275336 A1 * | 11/2008 | Deschamps et al. | 600/425 |

FOREIGN PATENT DOCUMENTS

| | | |
|---|---|---|
| DE | 10036143 C2 | 12/2003 |
| DE | 102004057308 A1 | 7/2006 |
| DE | 102005012700 A1 | 9/2006 |
| DE | 102005016472 A1 | 10/2006 |
| DE | 102005023743 A1 | 11/2006 |
| DE | 102005051102 A1 | 4/2007 |
| EP | 0679068 B1 | 3/2005 |

OTHER PUBLICATIONS

Siemens AG; AXIOM Artis dFA DynaCT A breakthrough in interventional 3D imaging; © 2005 Siemens Medical Solutions Order No. A91100-M1400-D159-10-7600 Printed in Germany; 1 Page; 91/4/6093 WS 04055; Others; 2005.
Internetseiten der Firma NewSight Corporation http://www.newsight.com; 7 Pages; Others; 2008.

* cited by examiner

*Primary Examiner* — Edward Glick
*Assistant Examiner* — Thomas R Artman

(57) ABSTRACT

The invention relates to a method for presenting interventional instruments in a 3D data set of an anatomy to be treated. A 3D data set of the anatomy is recorded before introduction of an interventional instrument. Once the interventional instrument has been applied, the spatial position of the instrument is determined by x-ray fluoroscopy from images created at two different angulations. A 3D model of the instrument is formed from the x-ray images. The 3D model of the instrument is fused with the 3D data set of the anatomy. A 3D hologram is reproduced from the fused 3D data set. The 3D hologram is repeatedly reproduced in real time to follow the application of the instrument in the presentation.

14 Claims, 3 Drawing Sheets

METHOD FOR REPRESENTING INTERVENTIONAL INSTRUMENTS IN A 3D DATA SET OF AN ANATOMY TO BE EXAMINED AS WELL AS A REPRODUCTION SYSTEM FOR PERFORMING THE METHOD

CROSS REFERENCE TO RELATED APPLICATIONS

This application claims priority of German application No. 10 2008 034 686.1 filed Jul. 25, 2008, which is incorporated by reference herein in its entirety.

FIELD OF THE INVENTION

The invention relates to a method for representing interventional instruments in a 3D data set of the anatomy to be examined. The invention further relates to a reproduction system for diagnostic imaging systems for performing the method for representing interventional instruments in a 3D data set of the anatomy to be examined.

BACKGROUND OF THE INVENTION

In medicine the switch from surgical interventions to minimally-invasive therapies is becoming established for serious illnesses.

Among the most frequent diseases with a fatal outcome are vascular angiopathies, with the resulting diseases such as heart attacks or strokes. The heart attack (myocardiac infarction=MI) is caused by diseases of the coronary vessels. In such cases arteriosclerotic plaque causes a thrombocyte activation and local thrombus formation. This can lead to a total occlusion ("blockage") of coronary vessels and thereby to a blocking of the blood flow. The occlusion in a heart attack is treated nowadays in the majority of cases by a minimally-invasive PCTCA (percutaneous transluminal coronary angioplasty). In this treatment the constricted points of the coronary artery are expanded with a "balloon catheter"

A further example of the switch from surgical to minimally-invasive therapy is characterized by the treatment of diseases of the heart valves. Until a few years ago replacement of heart valves involved an operation on an open heart. In this procedure mechanical or biological prosthetic heart valves (aortic valve, pulmonary valve) are implanted or the existing valve opening is surgically reshaped (mitral valve and tricuspidal valve). This was associated with high risks and long recuperation times of up to six weeks for the patient. For a few years now there have been methods of treating heart valve stenoses with the aid of special catheters.

Very important for a successful and low-risk minimally-invasive therapy is the 3D presentation of the anatomy to be treated, of an organ for example.

The disadvantage of the new minimally-invasive therapies is that they can only be performed with the aid of x-ray fluoroscopy. This previously only supplied 2D images of organs, of the heart for example and of the catheters or tools located there. This meant that a spatial assignment was barely possible.

Further developments in x-ray image processing have led to 3D presentations of vessels or cavities with the aid of contrast media.

It is known from a paper titled "AXIOM Artis FD Systems / DynaCT-A Breakthrough in Interventional 3D Imaging" by Patrick Kurp, a "Reprint from Medical Solutions, Jan. 2005, page 46-51", Order no. A91100-M1400-D105-1-7600, Reference CC 66105 SD 12043, that 3D soft tissue of non-moving organs can also be presented using x-ray technology. This type of method for 3D soft tissue creation, recognized in the medical imaging field as DynaCT imaging method, is described in DE 10 2004 057 308 A1, (which corresponds to U.S. Pat. No. 7,734,009) the content of which is included in this description. The term DynaCT (as capitalized) constitutes a registered trademark of the assignee of the present invention.

A distinct advance would be made with a C-arm x-ray apparatus currently being developed (CardDynaCT), with which images of 3D soft tissue and optionally high-contrast 3D images of the beating heart become possible by injecting contrast media.

Such a method is disclosed for example in DE 10 2005 016 472 A1, the contents of which is included in this description.

All known solutions however present the 3D x-ray images on 2D displays. The impression of a 3D image is achieved by volume rendering and rotation of the 3D image with the aid of a mouse of joystick.

With the aid of special eyeglasses, such as with polarization filters for example, it is possible to obtain an impression of a 3D image. However, this technology has not become established in medicine because of the additional eyeglasses required.

3D displays which manage without additional eyeglasses are known, made by companies such as newsight for example (see under http://www.newsight.com).

In these solutions the angles of view of the observer are detected and the polarization filter present in the display is controlled accordingly so that an impression of the 3D image is produced. This solution has the disadvantage that only one observer in each case perceives the impression of the 3D image. In addition the solution does not always operate reliably and has not established itself in the field of medical therapy.

A display system for image systems for reproducing medical images described in DE 100 36 143 C2, in which, instead of a display, a projector is used in the medical examination or intervention room, only allows 2D presentations however.

In the not yet published U.S. patent application Ser. No 11/093,561, "Creating a Stereoscopic Image Pair From Two Different Image Sources, Using Image Registration" a stereoscopic image impression is possible with the aid of two projectors and special eyeglasses worn by the observers. This solution has the advantage that a number of observers can see the 3D images; otherwise the disadvantages given above apply.

A method is described in the U.S. Pat. No. 6,672,165 B2 with which three-dimensional ultrasound images can be created holographically.

In the older DE 10 2008 015 312.5 a display system for reproducing medical hologram system is described in which the holographic images can be used for therapy, guidance and control. In practice however this is not a simple matter since many medical imaging systems, especially angiography systems, cannot generate any 3D data at a sufficiently high repetition rate in real time in order to make guidance possible. The known methods of 2D/3D overlaying are also not able to be used for holographic representation, so that it is not at all clear how such holographic images can be used for guiding an intervention.

DE 10 2005 051 102 A1 relates to a system and method for medical navigation, especially with C-arm and CT x-ray devices. In order to reduce the time outlay required for a medical navigation in percutaneous interventions, it is proposed to determine the position of a medical instrument in an object with the aid of projection images and to display the position in a three-dimensional structure image.

DE 10 2005 023 743 A1 describes a projection apparatus and a method for holographic reconstruction of scenes with a hologram matrix, an imaging system with a least one imaging means and an illumination system with sufficiently coherent light for illuminating a hologram encoded in the hologram matrix, with the light of the illumination device reconstructing the hologram. In a first step a reconstruction is undertaken as a Fourier transform of the encoded hologram in one plane of a first imaging means. In a second step the first imaging means forms an image of the hologram in a plane directly in front of the second imaging means. Simultaneously the second imaging means forms an image of the Fourier transform from the plane in an observer plane. In this way the reconstructed scene is provided enlarged in a reconstruction space stretched between the second imaging means and at least one observer window to at least one observer. The enlarged display of the hologram extends the size of the reconstruction space.

SUMMARY OF THE INVENTION

The underlying object of the invention is to specify a method of the type mentioned at the start, which makes possible a three-dimensional reconstruction of an instrunent together with a 3D data set. A further object of the invention is to embody a display system of the type mentioned at the start such that 3D image presentations at the correct location, i.e. in the immediate vicinity and in the correct spatial orientation relative to the patient, are made possible for faster and safer minimally-invasive therapy.

The object is achieved in accordance with the invention for a method for presentation of interventional instruments in a 3D data set of an anatomy to be treated by the following steps:
a) Recording a 3D data set of the anatomy to be treated before introducing an interventional instrument,
b) Once an interventional instrument has been applied, determining the spatial position of the instrument by means of x-ray fluoroscopy using two images created from two different angulations,
c) Forming a 3D model of the instrument,
d) Fusion of the 3D model of the instrument with the 3D data set of the anatomy concerned,
e) Reproduction of the fused 3D data set as a 3D hologram and
f) Repetition of steps b) through e) in real time, in order to follow the application of the instrument in the presentation.

The result of this is that real time data from a biplanar localization with a model of a localized instrument, determined from 3D data recorded once in a prior operation, is initially fused and subsequently presented holographically.

Inventively the fused 3D data set can be reproduced on a holographic display and/or by means of a holographic projector.

Advantageously the voxels of the 3D data set can be set to the 3D coordinates (3D model) of the instrument and can be given a specific color value.

It has proved advantageous for the 3D data set of the anatomy to be treated to be recorded by a diagnostic device from the group Magnetic Resonance Imaging (MRI), Computed Tomography, Positron Emission Tomography (PET) or Single Photon Emission Computed Tomography (SPECT). Alternately the 3D data set can have been recorded with DynaCT imaging system or Cardiac DynaCT imaging system in the interventional laboratory with C-arm devices.

Inventively a biplanar system with simultaneous fluoroscopy from two angulations can be employed.

Alternately a monoplanar system can be used, with the one plane being repeatedly moved back and forth between two angular positions.

The object is achieved inventively for a reproduction system for diagnostic image systems for executing the method for presenting interventional instruments in a 3D data set of the anatomy to be treated by at least one holographic imaging system being connected to the diagnostic imaging system, which reproduces a hologram of the fused 3D data set in an examination or intervention room.

Advantageously the reproduction apparatus can feature at least one holographic projection device and/or a holographic display.

It has proved advantageous for the holographic projection device to be assigned a hologram unit for creating a hologram matrix, which generates from a 3D data set control signals for a connected hologram projector for displaying the hologram.

Inventively the hologram unit can be integrated into the diagnostic image system.

Advantageously the hologram unit can create a hologram encoded in a hologram matrix, by the hologram matrix being illuminated by the hologram projector with coherent light for reproducing the hologram.

BRIEF DESCRIPTION OF THE DRAWINGS

The invention is explained in greater detail below with reference to exemplary embodiments shown in the drawing. The figures show.

DETAILED DESCRIPTION OF THE INVENTION

Figure 1:
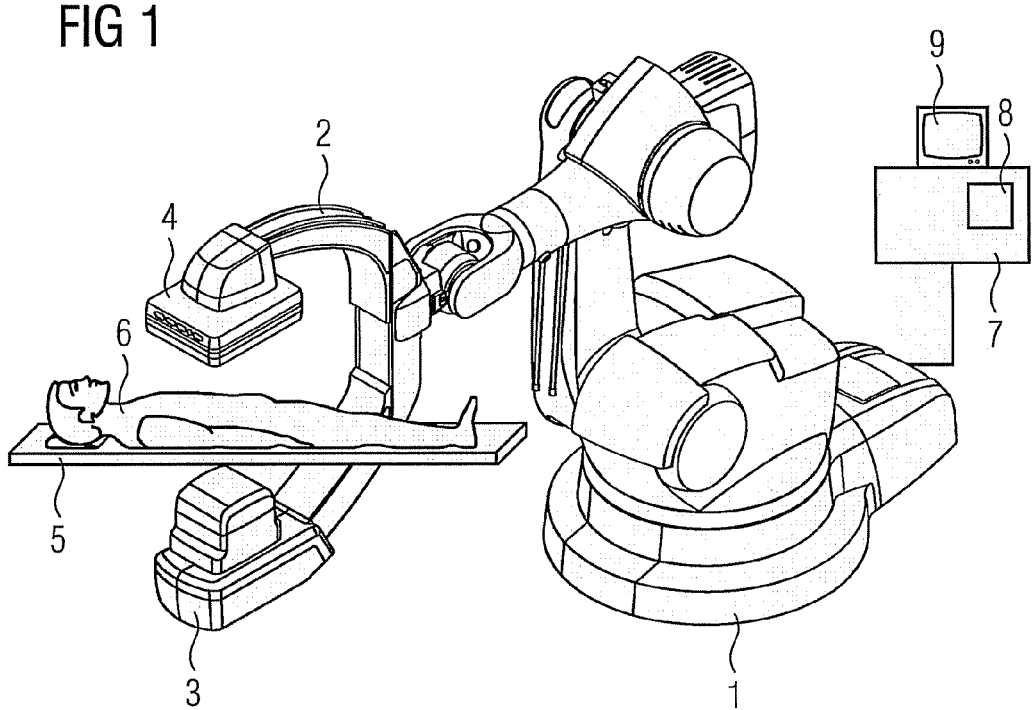
FIG. 1 a known C-arm x-ray system with an industrial robot as its carrier apparatus, FIG. 2 a view of the track of a detector and a radiation source as per FIG. 1 around an object to be examined in an axial direction of view, FIG. 3 an intervention room with an inventive projection apparatus and FIG. 4 a circuit layout of an inventive x-ray diagnostic device.

FIG. 1 shows an x-ray diagnostic device which has a C-arm able to be rotated on a stand in the form of an industrial robot 1, with an x-ray radiation source, for example an x-ray emitter 3, and an x-ray image detector 4 being attached to the ends of said C-arm.

The x-ray image detector 4 can be a rectangular or square, flat semiconductor detector which is preferably made of amorphous silicon (a-Si).

Located on a patient bed in the beam path of the x-ray emitter 3 is a patient to be examined so that an image of their heart can be recorded for example. Connected to the x-ray diagnostic device is a system control unit 7 with an image system 8, which receives and processes the image signals of the x-ray detector 4. The x-ray images can then be observed on a monitor 9.

By means of the industrial robot 1 known from DE 10 2005 012 700 A1 for example, which preferably has six axes of rotation and thus six degrees of freedom, the C-arm 2 can be repositioned as required, by being moved for example around a center of rotation between the x-ray emitter 3 and (including) the x-ray detector 4. The inventive x-ray system 1 to 4 is especially able to be rotated around centers of rotation and axes of rotation in the plane of the x-ray image detector 4, preferably around the center point of the x-ray image detector 4 and around the center point of the axes of rotation intersecting the center point of the x-ray image detector 4.

Figure 2:
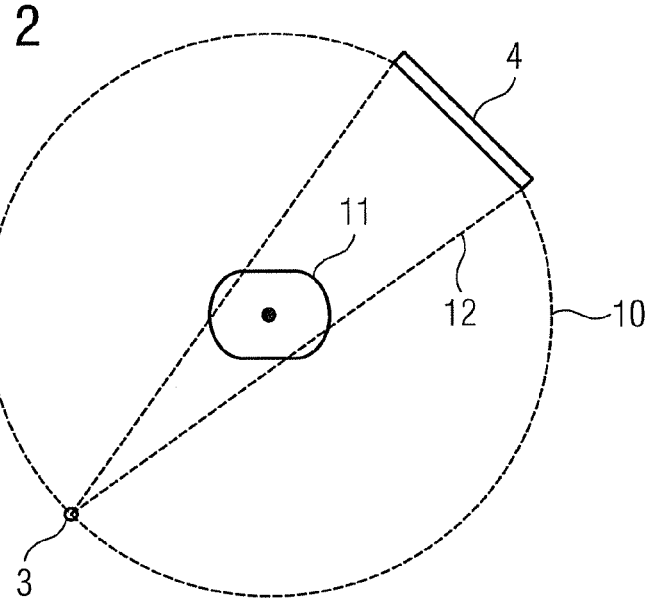

If in one example embodiment, 3D data sets are to be recorded using the foregoing DynaCT imaging method, the rotatably supported C-arm with x-ray emitter 3 and x-ray image detector 4 is rotated such that, as shown from above the axis of rotation schematically in FIG. 2, the x-ray emitter 3 illustrated here by way of its beam focus as well as the x-ray image detector 4 move around an object 11 to be examined on a planetary track 10. The planetary track 10 can be traveled completely or partly to create a 3D data set.

The C-arm 2 with x-ray emitter and x-ray image detector 4 moves in this case in accordance with the DynaCT method preferably around an angular area of at least 180°, for example 180° plus beam angle, and records projection images from different projections in rapid succession. The reconstruction can only be undertaken from one part area of this recorded data.

The object 11 to be examined can for example be the body of a human being or of an animal, but can also be a phantom body.

The x-ray emitter 3 emits a bundle of rays 12 emitted from the beam focus of its x-ray source, which hits the x-ray image detector 4.

The x-ray detector 3 and the x-ray image detector 4 each orbit around the object 5 so that the x-ray emitter 3 and the x-ray image detector 4 lie on opposite sides of the object 11.

In normal radiography or fluoroscopy by means of such an x-ray diagnostic device, the medical 2D data of the x-ray detector 4 is buffered if necessary in the image system 8 and subsequently reproduced on the monitor 9.

Figure 3:
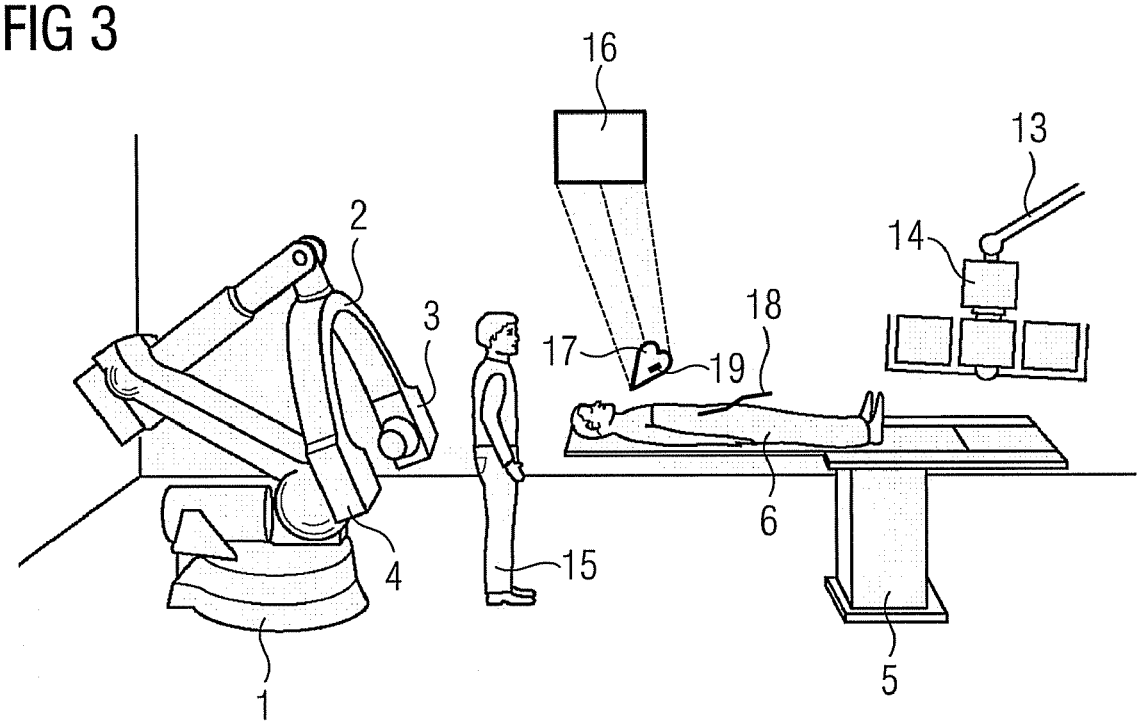

Shown in FIG. 3 is an examination or intervention room with the x-ray diagnostic device according to FIG. 1 which has a C-arm 2 mounted rotatably on an industrial robot 1 with x-ray emitter 3 and x-ray image detector 4. The patient 6 to be examined lies on the patient support bed 5. Mounted on an arm 13 is a rotatable and tiltable monitor array 14, consisting of a matrix of a number of flat-screen displays. A person conducting the examination or an operator 15, for example a doctor, stands at the head end of the patient support bed 5 and can observe the patient 6 as well as the monitor array 14 with the flat-panel displays.

Inventively a hologram projector 16 is typically mounted on the wall of the examination or intervention room and projects a hologram 17 of the 3D data set of the 3D image of the heart created as previously described. The hologram projector 16 can however also be mounted on an attachment device, such as an arm or an array, on the ceiling, on the wall or on the floor.

A heart catheter 18 can be inserted into the patient 6, the catheter tip 19 of which is reproduced in the hologram 17.

Figure 4:
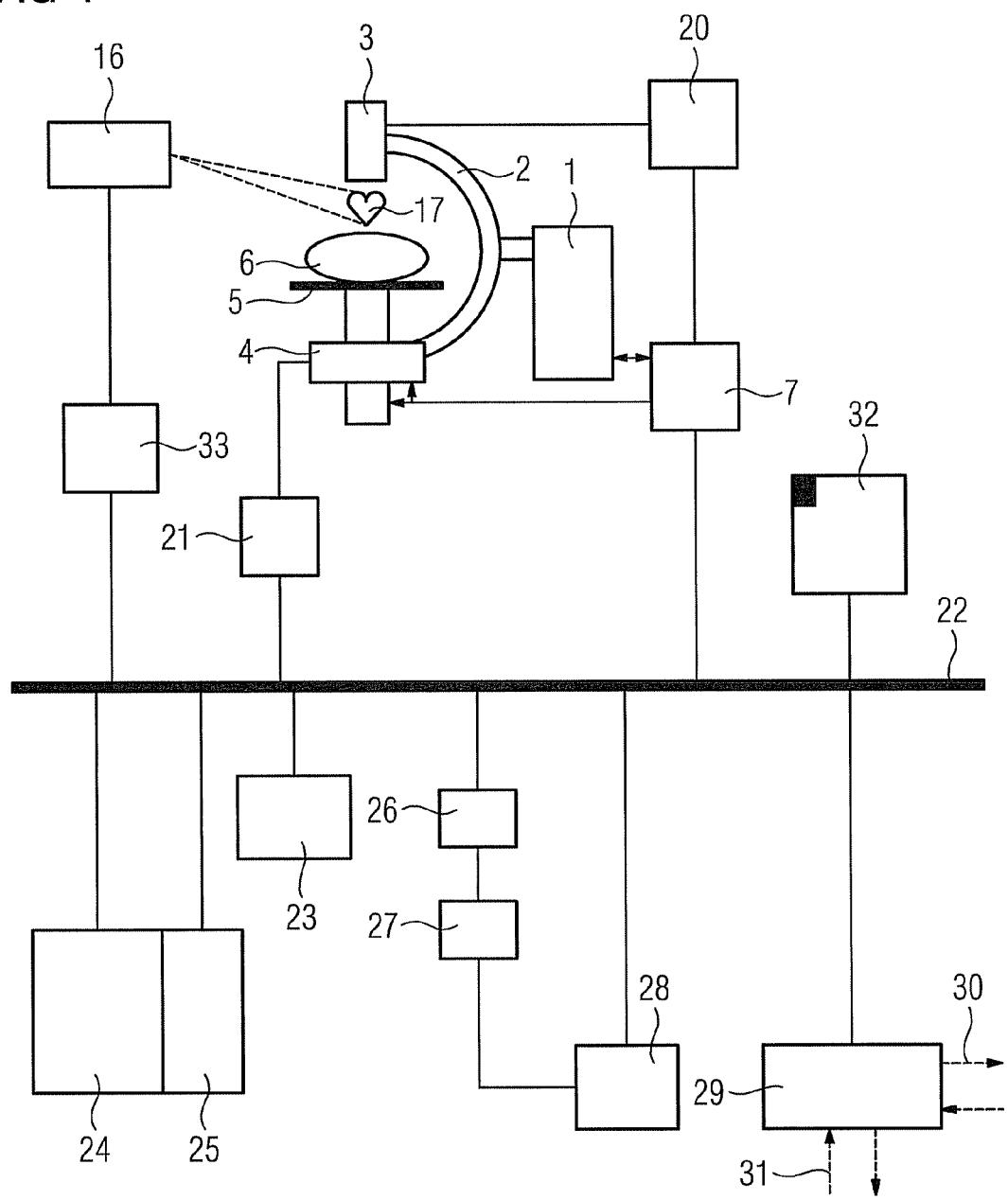

Shown in more detail in FIG. 4 is the circuit layout of the inventive x-ray diagnostic device.

A high-voltage generator 20 is connected to the system control unit 7 and drives the x-ray emitter 3. The system control unit 7 is furthermore connected to the x-ray image detector 4, for example the a-Si flat-panel detector, for synchronous control of the x-ray emitter 3 when the x-ray image detector 4 is ready to record an image. The system control unit 7 likewise for example controls the rotary motors of the C-arm 2 accommodated in the industrial robots 1 and records the acknowledgement of the position of the C-arm 2.

The image data read out of the x-ray detector 4 is processed in a pre-processing unit 21 and supplied to a system data bus for further distribution. The system control unit 7 and the pre-processing unit 21 can be a part of the imaging system 8. They can however also be realized as separate hardware or software.

The image data of the signals of the x-ray image detector 4 processed by the pre-processing unit 21 are supplied via the system data bus 22 to an image processing unit 23 for x-ray images with 3D and soft tissue processor. A 2D/3D display unit 24 forms a reproduction unit together with an input unit 25 (USER I/O).

Also connected to the system data bus 22 is a localization device 26, which, as will be explained below, detects objects in medical images. Connected to this localization unit 26 is a device for model creation 27 which determines a 3D model of the object detected in the medical image. The device for model creation 27 is also connected to an image fusion unit 28, which effects an overlaying of the 3D model of the detected object with the 3D data set. The output signals of the image fusion unit are fed to the 2D/3D display unit 25 for three-dimensional reproduction.

Connected to the system data bus 22 for communication with the outside world is a DICOM interface for patient and image data, which exchanges patient data over data lines with the HIS 30 and image data over further data lines 31 by means of the intranet of the hospital or over the Internet. Image data of other modalities, such as CT or MR images for example, can be retrieved via the further data lines 31.

An image data memory 32 is also connected to the system data bus 22 which buffers the image data supplied by the pre-processing unit 21, so that it can subsequently be retrieved by the image processing unit 23 and/or forwarded via the DICOM interface 29.

Typically connected to the system data bus 22 for 3D reproduction of a heart for example is a hologram unit 33 which creates from the 3D data set computed control signals for a connected hologram projector 16, so that the hologram 17 of the organ to be treated is reproduced at the correct location, i.e. in the immediate vicinity, and in the correct spatial orientation relative to the patient.

So that the heart catheter 18 and its catheter tip 19 can be reproduced in the hologram, pre-interventional 3D images are created with an x-ray diagnostic device in accordance with FIG. 1 for example, so that a 3D data set of a region of interest of the anatomy, for example the heart, is obtained. The DynaCT method known from FIG. 2 is used for this purpose. Instead of the DynaCT method the following methods can also be used:

Magnetic Resonance Imaging (MRI),
Computed Tomography (CT),
Ultrasound,
Positron Emission Tomography (PET),
Single Photon Emission Computed Tomography (SPECT),
Optical methods such as for example endoscopy and OCT and/or
Electromagnetically-generated images, generated by magnetic tracking for example.

After interventional instruments, such as needles, catheters, heart valves etc. have been inserted into the patient 6 by a doctor, these are followed in real time by means of biplanar localization, in which the patient is x-rayed by means of the x-ray system 1 through 4 from two different angulations, with the C-arm 2 swinging from a first angular position into a second angular position. Instead of the swinging back and forth of the x-ray system 1 with monoplane arrangement a detection of the position of the instruments from 2 planes can be undertaken by means of a biplanar system.

From the images recorded from two angles the spatial position of the instrument is determined by the localization device 26 by means of biplanar localization. The device for model creation 27 computes from the spatial positions of the instrument a 3D model of the instrument.

This 3D model of the instrument is overlaid in the image fusion unit 28 with the 3D data set of the antimony of interest, for example of the heart and sent via the 2D/3D display unit for reproduction to the hologram unit 33 for presentation of the hologram 17 by means of hologram projector 16 and/or a holographic display for example. During the fusion of the 3D model with the 3D data set in the simplest case for example the voxels of the 3D data set with the coordinates of the instrument (3D model) are replaced by a specific gray or color value.

The biplanar images are repeated continuously in real time so that the application of the instrument can be followed in the 3D hologram.

Inventively a holographic 3D image presentation in space is used for medical 3D imaging in medical minimally-invasive interventions, in which the 3D model of the instrument is reproduced in the 3D data set of the anatomy involved.

in such cases a PC-based technology can advantageously be used, which is known for example from SEEREAL TECHNOLOGIES S.A. (http://www.seereal.com/) for HDTV applications and is described in US 2006/0050340 A1, "Method and Device for Encoding and Reconstructing Computer-Generated Video Holograms", and DE 10 2005 023 743 A1 "Projektionsvorrichtung und Verfahren zur holographischen Rekonstruktion von Szenen" (Projection device and method for holographic reconstruction of scenes), the contents of which is included in the description.

A further advantage is the presentation, for example in 3D, of an organ to be treated in the immediate vicinity and in the correct spatial orientation relative to the patient.

The inventive method makes it possible for interventional instruments which are introduced during a therapy (interventions) into the human body to be displayed holographically jointly with the 3D data set.

The following steps are necessary to do this:

1) The 3D data set of the patient can originate from pre-interventional images, e.g. MRI, CT, PET, SPECT, etc. Alternately the 3D data set can also be recorded with DynaCT imaging system or Cardiac DynaCT imaging system in the interventional laboratory with C-arm devices. The important aspect here is that the 3D data set as a rule does not yet contain the interventional instrument. The application of interventional instruments (e.g. needles, catheters, heart valves etc.) is followed in real time with x-ray fluoroscopy.

2) The position of the instrument is detected from two planes. A biplanar system with simultaneous fluoroscopy from two angulations is advantageous for this. Alternately a monoplanar system can also be used, with the one plane being moved back and forth repeatedly between two angle positions. The spatial position of the instrument is determined using biplanar localization from the images taken from two angulations. The result produced is a 3D model of the instrument.

3) The next step is a fusion of the 3D model of the instrument with the 3D data set of the anatomy concerned. In the simplest case the voxels of the 3D data set are set to the coordinates (3D model) of the instrument and given a particular gray value (color).

4) The fused 3D data set can then be presented on a holographic display.

5) Steps 2) through 4) are repeated in real time in order to follow the application of the instrument in the 3D hologram.

In summary a method is described here that essentially consists of the following four steps:
1. Recording a 3D data set,
2. Localization of instruments by means of biplanar x-ray localization,
3. Fusion of the 3D data set with a model of the localized instrument and
4. Holographic visualization of the fused data.

The invention claimed is:

1. A method for presenting an interventional instrument in a 3D data set of an anatomy to be treated, comprising:
recording the 3D data set of the anatomy before introducing the interventional instrument;
recording fluoroscopy x-ray images of the anatomy from two different angulations after introducing the interventional instrument;
determining a spatial position of the interventional instrument by the x-ray images;
generating a 3D model of the interventional instrument from the x-ray images;
fusing the 3D model of the interventional instrument with the 3D data set of the anatomy;
reproducing a 3D hologram from the fused 3D data set for presenting the 3D model of the interventional instrument in the 3D data set of the anatomy; and
repeatedly reproducing the 3D hologram in real time to follow an application of the interventional instrument for the presentation.

2. The method as claimed in claim 1, wherein the 3D hologram is reproduced on a holographic display.

3. The method as claimed in claim 1, wherein the 3D hologram is reproduced by a holographic projector.

4. The method as claimed in claim 1, wherein voxels of the 3D data set of the anatomy are occupied by coordinates of the 3D model of the interventional instrument and are set to a specific color value.

5. The method as claimed in claim 1, wherein the 3D data set of the anatomy is recorded by a diagnostic device selected from the group consisting of: Magnetic Resonance Imaging, Computed Tomography, Positron Emission Tomography, and Single Photon Emission Computer Tomography.

6. The method as claimed in claim 1, wherein the 3D data set of the anatomy is recorded in an interventional laboratory with C-arm devices.

7. The method as claimed in claim 1, wherein the x-ray images are recorded by a biplanar system with simultaneous fluoroscopy from the two different angulations.

8. The method as claimed in claim 1, wherein the x-ray images are recorded by a monoplanar system with one plane being repeatedly moved back and forth between the two different angular positions.

9. A diagnostic image system, comprising:
an image recording device for:
recording a 3D data set of an anatomy to be treated before introducing an interventional instrument; and
recording fluoroscopy x-ray images of the anatomy from two different angulations after introducing the interventional instrument; and
a holographic reproduction device for:
determining a spatial position of the interventional instrument by the x-ray images;
generating a 3D model of the interventional instrument from the x-ray images;
fusing the 3D model of the interventional instrument with the 3D data set of the anatomy; and reproducing a 3D hologram from the fused 3D data set for presenting the 3D model of the interventional instrument in the 3D data set of the anatomy.

10. The diagnostic image system as claimed in claim 9, wherein the x-ray images of the anatomy after introducing the interventional instrument are repeatedly recorded and the 3D hologram is repeatedly reproduced in real time to follow an application of the interventional instrument for the presentation.

11. The diagnostic image system as claimed in claim 9, wherein the holographic reproduction device comprises a hologram projector and a holographic display.

12. The diagnostic image system as claimed in claim 11, wherein the hologram projector is connected to a hologram unit for creating a hologram matrix to present a hologram.

13. The diagnostic image system as claimed in claim 12, wherein the hologram unit is integrated into the diagnostic imaging system.

14. The diagnostic image system as claimed in claim 12, wherein the hologram unit creates the hologram encoded in the hologram matrix that is illuminated by the hologram projector with coherent light for reproducing the hologram.

* * * * *